US008097561B2

(12) United States Patent
Nabors et al.

(10) Patent No.: US 8,097,561 B2
(45) Date of Patent: Jan. 17, 2012

(54) HERBICIDAL COMPOSITION

(75) Inventors: James Nabors, Greensboro, NC (US);
Jeffrey Fowler, Greensboro, NC (US);
Michael Hopkinson, Greensboro, NC (US)

(73) Assignee: Syngenta Crop Protection, Inc., Greensboro, NC (US)

( * ) Notice: Subject to any disclaimer, the term of this patent is extended or adjusted under 35 U.S.C. 154(b) by 639 days.

(21) Appl. No.: 10/517,732

(22) PCT Filed: Jun. 4, 2003

(86) PCT No.: PCT/US03/17486
§ 371 (c)(1),
(2), (4) Date: Jun. 9, 2005

(87) PCT Pub. No.: WO03/105587
PCT Pub. Date: Dec. 24, 2003

(65) Prior Publication Data
US 2005/0233907 A1   Oct. 20, 2005

(51) Int. Cl.
*A01N 25/32* (2006.01)
*A01N 43/40* (2006.01)
*A01N 43/84* (2006.01)
*A01N 33/00* (2006.01)

(52) U.S. Cl. ......... 504/105; 504/130; 504/226; 504/326

(58) Field of Classification Search .................. 504/103, 504/129, 138, 139, 142, 261, 263, 267, 280, 504/289, 336, 341, 342, 310
See application file for complete search history.

(56) References Cited

U.S. PATENT DOCUMENTS

| | | | |
|---|---|---|---|
| 3,937,730 A | 2/1976 | Vogel et al. | |
| 4,150,968 A | 4/1979 | Synek et al. | |
| 5,002,606 A | 3/1991 | Moser et al. | |
| 5,457,085 A | 10/1995 | Seckinger et al. | |
| 5,700,759 A | 12/1997 | Caulder et al. | |
| 5,958,835 A | 9/1999 | Baker et al. | |
| 5,981,432 A | 11/1999 | Hudetz et al. | |
| 6,093,680 A * | 7/2000 | Gillespie et al. | 504/363 |
| 6,165,939 A | 12/2000 | Agbaje et al. | |
| 6,235,682 B1 | 5/2001 | Penner et al. | |
| 6,319,949 B1 | 11/2001 | Schussler et al. | |
| 6,333,022 B1 | 12/2001 | Tanaka | |
| 6,365,550 B1 | 4/2002 | Feucht et al. | |
| 2003/0096708 A1* | 5/2003 | Agbaje et al. | 504/365 |

FOREIGN PATENT DOCUMENTS

| | | |
|---|---|---|
| EP | 0070702 | 1/1983 |
| EP | 0244754 | 11/1987 |
| EP | 1344454 | 9/2003 |
| GB | 986911 | 3/1965 |
| JP | 8217605 | 8/1996 |
| JP | 8291001 | 11/1996 |
| WO | WO 9117657 | 11/1991 |
| WO | WO 9526631 | 10/1995 |
| WO | 97/34485 | 9/1997 |
| WO | WO 0003595 | 1/2000 |
| WO | 02/32227 | 4/2002 |
| WO | WO 0249429 | 6/2002 |
| WO | WO 02071846 | 9/2002 |

OTHER PUBLICATIONS

The Agrochemical Handbook, 3rd Edition, A0278/Aug. 1991.*
Foy, Chester L., Department of Plant Pathology, Physiology and Weed Science, Virginia Polytechnic Institute and State University; "Progress and Development in Adjuvant Use Since 1989 in the USA"; *Pesticide Science*, 1993, 38, pp. 65-76.
Frisch, P.D. and Verbelen, R.A., "Dearomatized Tailor Made Hydrocarbon Fluids in Pesticide Formulations", *Pesticide Formulations and Application Systems: 18th* vol. STP 1347, J.D. Nalewaja, G.R. Goss, and R.S. Tann, Eds., American Society for Testing and Materials, 1998.
Krenek, Michael R. and Rohde, William H., "An Overview—Solvents for Agricultural Chemicals", *Pesticide Formulations and Application Systems: 8th* vol. ASTM STP 980, D.A. Hovde and G.B. Beestman, Eds., American Society for Testing and Materials, Philadelphia, 1988.
Barrentine, J.L. and Warren, G.F., "Isoparaffinic Oil as a Carrier for Chlorpropham and Terbacil", *Weed Science* (1970), 18(3), 365-72; CODEN: WEESA6 ISSN:0043-1745. CAN 73:44157 AN 1970:444157 Caplus.
Burr, R.J. and Warren, G.F., "Enhancement of Herbicide Activity with an Isoparaffinic Oil Carrier", *Weed Science* (1971) Issue 6, Nov. 1971, pp. 701-705.
Jordan, T.N. and Warren, G.F., "Effects of Prometryn and Dinoseb Combinations in an Undiluted Oil Carrier", *Weed Science* (1975) vol. 23, Issue 4, Jul. 1975, pp. 328-332.
Burr, R.J. and Warren, G.F., "Selectivity of Dinoseb in an Isoparaffinic Oil Carrier", *Weed Science* (1971) vol. 19, Issue 6, Nov. 1971, pp. 706-708.
Burr, R.J. and Warren, G.F., "An Oil Carrier for Increasing Purple Nutsedge Control", *Weed Science* (1972) vol. 20, Issue 4 Jul. 1972, pp. 324-327.

* cited by examiner

*Primary Examiner* — Alton Pryor
(74) *Attorney, Agent, or Firm* — James Cueva

(57) ABSTRACT

A herbicidal composition comprising, in addition to customary inert formulation excipients, as a mixture of at least one acetamide herbicide and a lipophilic additive comprising at least one member selected from the group consisting of C13-C20 fatty acids, C13-C20 fatty alcohols and hydrocarbon fluids.

13 Claims, No Drawings

HERBICIDAL COMPOSITION

BACKGROUND OF THE INVENTION

The present invention relates to novel herbicidal synergistic compositions containing a combination of at least one acetamide herbicide and at least one lipophilic additive suitable for selectively controlling weeds in crops of cultivated plants, typically in crops of cereals, rape, sugar beet, sugar cane, rice, maize, plantation crops, soybeans and cotton.

The invention further relates to a method for controlling weeds in crops of cultivated plants and to the use of said novel composition therefor.

BRIEF SUMMARY OF THE INVENTION

Acetamides are a known class of selective herbicides. Acetamides, as used herein, include those classes of herbicides commonly referred to as acetamides as well as chloroacetamides and oxyacetamides.

Surprisingly, it has now been found that combinations of at least one acetamide herbicide and at least one lipophilic additive exert a synergistic effect that is able to control the majority of weeds preferably occurring in crops of cultivated plants, without substantial injury to the cultivated plants.

Lipophilic additives suitable for use in the present invention include C13-C20 fatty acids, C13-C20 fatty alcohols and hydrocarbon fluids as defined herein.

Further, the compositions of the present invention perform more consistently across varying environmental conditions compared to similar formulations absent the lipophilic additive.

DETAILED DESCRIPTION OF THE INVENTION

The present invention provides a novel synergistic composition for the selective control of weeds that, In addition to customary inert formulation excipients, comprises as active ingredients a mixture of
a) at least one acetamide herbicide
and
b) a synergistically effective amount of a lipophilic additive comprising at least one member selected from the group consisting of C13-C20 fatty acids, C13-C20 fatty alcohols and hydrocarbon fluids.

Representative acetamide herbicides include diphenamid, napropamide, naproanilide, acetochlor, alachlor, butachlor, dimethachlor, dimethenamid, dimethenamid-P, fentrazamide metazachlor, metolachlor, pethoxamid, pretilachlor, propachlor, propisochlor, S-metolachlor, thenylchlor, flufenacet and mefenacet. As used herein, the term acetamide includes mixtures of the two or more acetamides as well as mixtures of optical isomers of the acetamides. For example, mixtures of the (R) and (S) isomers of metolachlor wherein the ratio of (S)-2-chloro-N-(2-ethyl-6-methylphenyl)-N-(2-methoxy-1-methylethyl)acetamide to (R)-2-chloro-N-(2-ethyl-6-methylphenyl)-N-(2-methoxy-1-methylethyl)acetamide is in the range of from 50-100% to 50-0%, preferably 70-100% to 30-0% and more preferably 80-100% to 20-0%.

The lipophilic additives of the present invention comprise at least one member selected from the group consisting of C13-C20 fatty acids, C13-C20 fatty alcohols and hydrocarbon fluids. In a preferred embodiment, the lipophilic additives are saturated. Preferred fatty acids include stearic acid. A preferred fatty alcohol is stearyl alcohol. The hydrocarbon fluids suitable for use as the lipophilic additives of the present invention include mixtures of paraffins, naphthenes and aromatics.

Preferably, the hydrocarbon fluids contain less than 2.0 wt. %, more preferably 0.5 wt. % or less, most preferably 0-0.2 wt. % aromatic component. Preferred hydrocarbon fluids contain greater than 50 wt. % paraffins. Preferably 50-100 wt. %, more preferably 90-100 wt. % of the paraffins present are iso-paraffins. Preferably, at least 95 wt. %, more preferably at least 98 wt. %, of the carbon structures of the hydrocarbon fluids have a carbon number distribution from C13 to C20. Preferred hydrocarbon fluids have an initial boiling point of at least 200° C., preferably at least 250° C. and a final boiling point of 325° C. or less.

Preferred hydrocarbon fluids for use in the present invention contain less than 2.0 wt. %, more preferably 0.5 wt. % or less, most preferably 0-0.2 wt. % aromatic component; greater than 50 wt. % paraffins and 50-100 wt. %, more preferably 90-100 wt. % of the paraffins present are iso-paraffins.

More preferred hydrocarbon fluids for use in the present invention contain less than 2.0 wt. %, more preferably 0.5 wt. % or less, most preferably 0-0.2 wt. % aromatic component; greater than 50 wt. % paraffins; 50-100 wt. %, more preferably 90-100 wt. % of the paraffins present are iso-paraffins and at least 95 wt. %, more preferably at least 98 wt. %, of the carbon structures of the hydrocarbon fluids have a carbon number distribution from C13 to C20.

Still more preferred hydrocarbon fluids for use in the present invention contain less than 2.0 wt. %, more preferably 0.5 wt. % or less, most preferably 0-0.2 wt. % aromatic component; greater than 50 wt. % paraffins; 50-100 wt. %, more preferably 90-100 wt. % of the paraffins present are Iso-paraffins; at least 95 wt. %, more preferably at least 98 wt. %, of the carbon structures of the hydrocarbon fluids have a carbon number distribution from C13 to C20; an initial boiling point of at least 200° C., preferably at least 250° C. and a final boiling point of 325° C. or less.

Particularly preferred hydrocarbon fluids for use as the lipophilic additives of the present invention are synthetic iso-paraffin fluids such as Isopar® V available from Exxon Chemical Company.

The lipophilic additives of the present invention are not generally thought of as herbicides. Therefore, it is entirely surprising that the combination of the acetamides with the lipophilic additives exceeds the expected action against the weeds to be controlled and thus in particular enhances the activity range of the acetamides in two respects: On the one hand, the concentration of the acetamide herbicide is reduced while the effectiveness of said herbicide is retained. On the other hand, the novel herbicidal composition also achieves a high degree of weed control where the single compounds have become no longer agriculturally effective at low concentrations. The consequence is a substantial broadening of the activity spectrum against weeds and an additional increase in the selectivity for the cultivated plants that is necessary and desirable in the event of unintentional overapplication of herbicide. In addition, the novel composition permits greater flexibility with respect to subsequent crops while retaining the excellent control of weeds in crops of cultivated plants.

The composition of the invention may be used against a large number of agronomically important weeds, including *Stellaria, Nasturtium, Agrostis, Digitaria, Avena, Setaria, Sinapis, Lolium, Solanum, Phaseolus, Echinochloa, Scirpus, Monochoria, Sagittaria, Bromus, Alopecurus, Sorghum halepense, Rottboellia, Cyperus, Abutilon, Sida, Xanthium,*

*Amaranthus, Chenopodium, Ipomoea, Chrysanthemum, Galium, Panicum, Brachiara, Viola,* and *Veronica*. For purposes of the present invention, the term "weeds" includes undesirable crop species such as volunteer crops. The compositions of the invention are preferably used in soil-applied preemergence applications. The composition of the invention is suitable for selectively controlling weeds in crops of cultivated plants, typically cereals, rape, sugar beet, sugar cane, rice, maize, plantation crops and in crops of soybeans and cotton. Crops of cultivated plants will also be understood as meaning those crops that have been made tolerant to herbicides or classes of herbicides by conventional plant breeding or genetic engineering methods (for example transgenic crops).

The composition of the invention contains the acetamide herbicide and the lipophilic additive in a ratio (wt/wt) of 90:1 to 1.5:1. Preferred ratios of the acetamide to the lipophilic additives are 60:1 to 5:1.

It has been found that particularly effective compositions are those of metolachlor including mixtures containing the optical isomers of metolachlor, for example S-metolachlor, with the hydrocarbon fluid lipophilic additives. Preferred acetamides include mixtures of metolachlor (S) and (R) isomers wherein the ratio of (S)-2-chloro-N-(2-ethyl-6-methylphenyl)-N-(2-methoxy-1-methylethyl)acetamide to (R)-2-chloro-N-(2-ethyl-6-methylphenyl)-N-(2-methoxy-1-methylethyl)acetamide is in the range of from 50-100% to 50-0%, preferably 70-100% to 30-0% and more preferably 80-100% to 20-0%.

The compositions of the present invention may contain co-herbicides. Co-herbicides suitable for use in the present invention include PSII inhibitors, PSI inhibitors, ALS inhibitors, HPPD inhibitors, ACCase inhibitors, Cell Division inhibitors, PDS inhibitors, lipid metabolism inhibitors and PPGO inhibitors. Representative co-herbicides include atrazine, halosulfuron-methyl, terbuthylazine, dicamba, fluthiacet-methyl, pyridate, butafenacil, NOA 402989, terbutryn, simazine, prosulfuron, primisulfuron, imazapyr, sethoxydim, flufenacet, cloransulam, diclosulam, metribuzin, isopropazol, isoxaflutole, iodosulfuron-methyl-sodium, isoxachlortole, sulfentrazone, mesotrione, flurtamone, sulcotrione, azafenidin, metosulam, flumetsulam, florasulam, pendimethalin, trifluralin, MON4660, 8-(2,6-diethyl-4-methylphenyl)-tetrahydropyrazolo[1,2-d][1,4,5]oxadiazepine-7,9-dione, 4-Hydroxy-3-[2-(2-methoxyethoxymethyl)-6-trifluoromethylpyridine-3-carbonyl]-bicyclo[3.2.1]oct-3-en-2-one, flumiclorac-pentyl, bentazone, AC304415, bromoxynil, BAS145138, nicosulfuron, cyanazine, rimsulfuron, imazaquin, amitrole, thifensulfuron, thifensulfuron-methyl, bilanafos, metobenzuron, diuron, MCPA, MCPB, MCPP, 2,4-D, diflufenzopyr, clopyralid, clopyralid-olamine, fluroxypyr, quinmerac, dimethametryn, esrocarb, pyrazosulfuron-ethyl, benzofenap, clomazone, carfentrazone-ethyl, butylate, EPTC, aclonifen, fomesafen, flumioxazin, paraquat, glyphosate, glufosinate, S-glufosinate, sulfosate, imazamox, imazethapyr and the agriculturally acceptable salts and esters thereof.

It has been found that particularly effective mixtures of active ingredients include the following combinations:
acetamide+atrazine, acetamide+glyphosate,
acetamide+atrazine+glyphosate, acetamide+metribuzin,
acetamide+mesotrione, acetamide+prometryn, acetamide+quinmerac,
acetamide+dimethametryn, acetamide+esprocarb,
acetamide+pyrazosulfuron-ethyl, acetamide+benzofenap,
acetamide+pendimethalin, acetamide+terbuthylazine and
acetamide+4-Hydroxy-3-[2-(2-methoxyethoxymethyl)-6-trifluoromethylpyridine-3-carbonyl]-bicyclo[3.2.1]oct-3-en-2-one.

Preferred amongst these combinations of active ingredients are those wherein the acetamide comprises at least one member selected from the group consisting of acetochlor, alachlor, dimethenamid, dimethenamid-P, metolachlor, S-metolachlor, fentrazamide, pethoxamid, flufenacet and mefenacet.

In addition to the acetamide herbicide, the lipophilic additive and optionally at least one compound from amongst the co-herbicides set forth above, the synergistic compositions according to the invention may contain at least one safener. Suitable safeners include benoxacor, cloquintocet, dichlormid, fenclorim, flurazole, fluxofenim, furilazole, mefenpyr and the agriculturally acceptable salts and esters thereof such as cloquintocet-mexyl and mefenpyr-diethyl. Particulary preferred safeners include benoxacor.

The abovementioned acetamides, co-herbicides and safeners are described and characterized in "The Pesticide Manual", Twelfth Edition, 2000, Crop Protection Publications or in other customary agronomical publications.

The rate of application can vary within a wide range and will depend on the nature of the soil, the type of application (application to the seed furrow; no-tillage application etc.), the crop plant, the weed to be controlled, the prevailing climatic conditions, and on other factors governed by the type and timing of application and the target crop. In general, the mixture of active ingredients according to the invention can be applied in a rate of application of 300 to 4,000 g of mixture of active ingredients/ha.

The co-herbicides and safeners may be applied to the plants, plant parts, seeds or locus thereof at the same time or at separate times as the acetamide/lipophilic additive mixtures of the present invention.

The present invention is also directed to a method of controlling undesired plant growth in the presence of cultivated plants, which comprises treating the cultivated plants, plant parts, seed or the locus thereof with a herbicidally effective amount of at least one acetamide herbicide and at least one lipophilic additive as described herein.

In the composition according to the invention, the weight ratio of the acetamide to at least one compound from amongst the co-herbicides set forth above is from 1:10 to 1:0.001.

If the composition comprises a safener, the weight ratio of acetamide to safener is preferably 5:1 to 30:1.

The composition of the present invention can be formulated in a variety of ways. For example, it can take the physical form of a dustable powder, gel, a wettable powder, a water dispersible granule, a water-dispersable or water-foaming tablet, a briquette, an emulsifiable concentrate, a microemulsifiable concentrate, an oil-in-water emulsion, a water-in-oil emulsion, a dispersion in water, a dispersion in oil, a suspoemulsion, a soluble liquid (with either water or an organic solvent as the carrier), an impregnated polymer film, or other forms known in the art. These formulations may be suitable for direct application or may be suitable for dilution prior to application, said dilution being made either with water, liquid fertilizer, micronutrients, biological organisms, oil or solvent. The compositions are prepared by admixing the active ingredient with adjuvants including diluents, extenders, carriers, and conditioning agents to provide compositions in the form of finely-divided particulate solids, granules, pellets, solutions, dispersions or emulsions. Thus, it is believed that the active ingredient could be used with an adjuvant such as a finely-divided solid, a mineral oil, a liquid of organic origin, water, various surface active agents or any suitable combination of these.

The active ingredient may also be contained in very fine microcapsules in polymeric substances. Microcapsules typically contain the active material enclosed in an inert porous shell which allows escape of the enclosed material to the surrounds at controlled rates. Encapsulated droplets are typically about 0.1 to 500 microns in diameter. The enclosed material typically constitutes about 25 to 95% of the weight of the capsule. The active ingredient may be present as a monolithic solid, as finely dispersed solid particles in either a solid or a liquid, or it may be present as a solution in a suitable solvent. Shell membrane materials include natural and synthetic rubbers, cellulosic materials, styrene-butadiene copolymers, polyacrylonitriles, polyacrylates, polyesters, polyamides, polyureas, polyurethanes, other polymers familiar to one skilled in the art, chemically-modified polymers and starch xanthates. Alternative very fine microcapsules may be formed wherein the active ingredient is dispersed as finely divided particles within a matrix of solid material, but no shell wall surrounds the microcapsule.

Suitable agricultural adjuvants and carriers that are useful in preparing the compositions of the invention are well known to those skilled in the art.

The formulations, i.e., the acetamides and the lipophilic additives and where applicable the agents, preparations, or compositions containing one or more than one liquid or solid formulation excipient are prepared in a known manner, e.g., by homogeneously mixing and/or grinding the compounds with said formulation assistants, typically liquid carriers or solid carriers.

The compositions of the present invention may be prepared by incorporating the lipophilic additive into a pre-mix or concentrate with the acetamide or adding the lipophilic additive and the acetamide separately as a tank mix when the product is diluted into, for example, water prior to application.

Liquid carriers that can be employed include water, toluene, xylene, petroleum naphtha, crop oil, acetone, methyl ethyl ketone, cyclohexanone, acetic anhydride, acetonitrile, acetophenone, amyl acetate, 2-butanone, chlorobenzene, cyclohexane, cyclohexanol, alkyl acetates, diacetonalcohol, 1,2-dichloropropane, diethanolamine, p-diethylbenzene, diethylene glycol, diethylene glycol abietate, diethylene glycol butyl ether, diethylene glycol ethyl ether, diethylene glycol methyl ether, N,N-dimethyl formamide, dimethyl sulfoxide, 1,4-dioxane, dipropylene glycol, dipropylene glycol methyl ether, dipropyleneglycol dibenzoate, diproxitol, alkyl pyrrolidinone, ethyl acetate, 2-ethyl hexanol, ethylene carbonate, 1,1,1-trichloroethane, 2-heptanone, alpha pinene, d-limonene, ethylene glycol, ethylene glycol butyl ether, ethylene glycol methyl ether, gamma-butyrolactone, glycerol, glycerol diacetate, glycerol monoacetate, glycerol triacetate, glycerol triacetate, hexadecane, hexylene glycol, isoamyl acetate, isobornyl acetate, isooctane, isophorone, isopropyl benzene, isopropyl myristate, lactic acid, laurylamine, mesityl oxide, methoxy-propanol, methyl isoamyl ketone, methyl isobutyl ketone, methyl laurate, methyl octanoate, methyl oleate, methylene chloride, m-xylene, n-hexane, n-octylamine, octyl amine acetate, oleylamine, o-xylene, phenol, polyethylene glycol (PEG400), propionic acid, propylene glycol, propylene glycol monomethyl ether, propylene glycol mono-methyl ether, p-xylene, toluene, triethyl phosphate, triethylene glycol, xylene sulfonic acid, trichloroethylene, perchloroethylene, ethyl acetate, amyl acetate, butyl acetate, propylene glycol monomethyl ether and diethylene glycol monomethyl ether, methanol, ethanol, isopropanol, and higher molecular weight alcohols such as amyl alcohol, tetrahydrofurfuryl alcohol, hexanol, octanol, etc., ethylene glycol, propylene glycol, glycerine, N-methyl-2-pyrrolidinone, and the like. Water is generally the carrier of choice for the dilution of concentrates.

Suitable solid carriers include talc, titanium dioxide, pyrophyllite clay, silica, attapulgite clay, kieselguhr, chalk, diatomaceous earth, lime, calcium carbonate, bentonite clay, Fuller's earth, cotton seed hulls, wheat flour, soybean flour, pumice, wood flour, walnut shell flour, lignin, and the like such as described in the CFR 180.1001. (c) & (d).

A broad range of surface-active agents are advantageously employed in both solid and liquid compositions, especially those designed to be diluted with carrier before application. Depending on the herbicides to be formulated, suitable surface-active compounds are nonionic, cationic and/or anionic surfactants and surfactant mixtures having good emulsifying, dispersing and wetting properties. Examples of suitable surfactants and surfactant mixtures are given in U.S. Pat. Nos. 5,958,835; 6,063,732 and 6,165,939, the disclosures of which are incorporated fully herein by reference. Also the surfactants customarily used for the art of formulation and described, inter alia, in "Mc Cutcheon's Detergents and Emulsifiers Annual" MC Publishing Corp., Ridgewood N.J., 1981, Stache, H., "Tensid-Taschenbuch" (Handbook of Surfactants), Carl Hanser Verlag, Munich/Vienna, 1981, and M. and J. Ash, "Encyclopedia of Surfactants", Vol I-III, Chemical Publishing Co., New York, 1980-81 are suitable for manufacture of the herbicides according to the invention.

The anionic surfactants suitable for use in the invention may be any known in the art. The anionic surfactants may be polyarylphenol polyalkoxyether sulfates and/or phosphates; $C_{8-18}$ alcohol polyalkoxyether phosphates, carboxylates, and/or citrates; alkyl benzenesulfonic acids; $C_{8-20}$ alkyl carboxylates including fatty acids; $C_{8-20}$ alcohol sulfates; $C_{8-20}$ alcohol phosphate mono- and diesters; $C_{8-20}$ alcohol and ($C_{8-20}$ alkyl)phenol polyoxyethylene ether carboxylates, sulfates and sulfonates; $C_{8-20}$ alcohol and ($C_{8-20}$ alkyl)phenol polyoxyethylene phosphate mono- and diesters; $C_{8-20}$ alkylbenzene sulfonates, naphthalene sulfonates and formaldehyde condensates thereof; lignosulfonates; $C_{8-20}$ alkyl sulfosuccinates and sulfosuccinamates; $C_{8-20}$ acyl glutamates, sarcosinates, isethionates and taurates; water-soluble soaps and mixtures thereof.

Exemplary polyarylphenol polyalkoxyether sulfates and phosphates include polyarylphenol polyethoxyether sulfates and phosphates, polyarylphenol polypropoxyether sulfates and phosphates, polyarylphenol poly(ethoxy/propoxy)ether sulfates and phosphates, and salts thereof. The term "aryl" includes, for example, phenyl, tolyl, naphthyl, tetrahydronaphthyl, indanyl, indenyl, styryl, pyridyl, quinolinyl, and mixtures thereof. Exemplary polyarylphenol polyethoxyether sulfates and phosphates include distyrylphenol polyethoxyether sulfates and phosphates, and tristyrylphenol polyethoxyether sulfates and phosphates. The polyarylphenol polyalkoxether sulfates and phosphates may have a degree of alkoxylation (e.g., ethoxylation) of between about 1 and about 50, preferably between about 2 and about 40, more preferably between about 5 and about 30. Commercially available polyarylphenol polyalkoxyether sulfates and phosphates include, for example, SOPROPHOR® 4 D 384 (Rhodia Corporation, Cranbury, N.J.) (tristyrylphenol $(EO)_{16}$ sulfate ammonium salt), SOPROPHOR® 3 D 33 (Rhodia Corporation, Cranbury, N.J.) (tristyrylphenol $(EO)_{16}$ phosphate free acid), SOPROPHOR® FLK (Rhodia Corporation, Cranbury, N.J.) (tristyrylphenol $(EO)_{16}$ phosphate potassium salt), DEHSCOFIX® 904 (Albright & Wilson Americas, Inc., Glen Allen, Va.) (tristyrylphenol polyethoxylated ether phosphate triethanolamine salt) and SOPROPHOR® RAM/384 (tristyrylphenol polyethoxylated ether sulfate neutralized with polyethoxylated oleylamine). In other embodiments, the polyarylphenol polyalkoxyether sulfates and phosphates may be mono-arylphenol polyalkoxyether sulfates and phosphates, such as styrylphenol polyethoxyether sulfates and phosphates.

Exemplary $C_{8-18}$ alcohol polyethoxyether phosphates, carboxylates and citrates include STEPFAC® 8180 (Stepan Corporation, Northfield, Ill.) (tridecylalcohol $(EO)_3$ phosphate), STEPFAC® 8181 (Stepan Corporation, Northfield, Ill.) (tridecylalcohol $(EO)_6$ phosphate), STEPFAC® 8182 (Stepan Corporation, Northfield, Ill.) (tridecylalcohol $(EO)_{12}$ phosphate), EMCOL® CN-6 (CK Witco Corporation, Greenwich, Conn.) (tridecylalcohol $(EO)_6$ carboxylate). The $C_{8-18}$ alcohol polyethoxyether phosphates, carboxylates and citrates may have a degree of ethoxylation of between about 1 and about 25, preferably between about 1 and about 20.

Exemplary alkylbenzene sulfonic acids and salts thereof Include dodecylbenzene sulfonic acid, and metal (for example sodium or calcium), ammonia or amine salts of the alkylbenzene sulfonic acids, including dodecylbenzene sulfonic acid. Amine neutralized versions include primary amines, diamines, triamines and alkanol amines.

Additional preferred anionic surfactants include ($C_{8-12}$ alkyl)phenol polyoxyethylene ether sulfates, and ($C_{8-12}$ alkyl)phenol polyoxyethylene phosphate mono- and diesters, accompanied in each case by monovalent counterions. In one embodiment the monovalent counterion for a ($C_{8-12}$ alkyl) phenol polyoxyethylene ether sulfate or a ($C_{8-12}$ alkyl)phenol polyoxyethylene phosphate is a protonated polyoxyethylene $C_{12-20}$ alkylamine surfactant. More specifically, polyoxyethylene tallowamine salt of a nonylphenol polyoxyethylene ether sulfate, nonylphenol polyoxyethylene phosphate, and a blend of such nonylphenol polyoxyethylene phosphate with polyoxyethylene tallowamine.

Suitable water-soluble soaps are the alkali metal salts, alkaline earth metal salts, ammonium salts or substituted ammonium salts of higher fatty acids ($C_{10}$-$C_{22}$), e.g. the sodium or potassium salts of oleic or stearic acid, or of natural fatty acid mixtures which can be obtained, inter alia, from coconut oil or tallow oil. Further suitable soaps are also the fatty acid methyl taurin salts.

The anionic surfactants are optionally neutralized with a basic compound. The basic compounds may be any known in the art that are capable of neutralizing the anionic surfactants. Basic compounds include, for example, inorganic bases, $C_{8-18}$ alkyl amine polyalkoxylates, alkanol amines, alkanol amides, and mixtures thereof.

Exemplary inorganic bases include ammonium hydroxides, sodium hydroxides, potassium hydroxides, calcium hydroxides, magnesium hydroxides, zinc hydroxides, and mixtures thereof. The $C_{8-18}$ alkyl amine polyalkoxylates may be, for example, $C_{8-18}$ alkyl amine polypropoxylates and/or $C_{8-18}$ alkyl amine polyethoxylates. Exemplary $C_{8-18}$ alkyl amine polyalkoxylates include tallow amine polyalkoxylates, cocoamine polyalkoxylates, oleylamine polyalkoxylates, and stearylamine polyalkoxylates. The $C_{8-18}$ alkyl amine polyethoxyates may have from about 2 to about 50 moles of ethylene oxide per molecule, more preferably from about 2 to about 20 moles of ethylene oxide per molecule. Exemplary $C_{8-18}$ alkyl amine polyethoxylates include tallow amine ethoxylates (2 moles EO or 8 moles EO), cocoamine ethoxylates, oleylamine ethoxylates, and stearylamine ethoxylates. Exemplary alkanol amines include diethanol amine and triethanol amine. Exemplary alkanol amides include oleic diethanolamide and linoleic diethanolamide, and the diethanolamides of other $C_{8-18}$ fatty acids.

The anionic surfactants may be neutralized to the inflection point in the titration curve with one or more basic compounds. One skilled in the art will recognize that the pH of the inflection will vary according to the acid and base strengths of the components being used, but will generally fall within the range of about pH 4 to about pH 9, preferably about pH 5 to about pH 7. For example, the compositions of the invention may comprise at least one polyarylphenol polyalkoxyether sulfate, polyarylphenol polyalkoxyether phosphate, $C_{8-18}$ alcohol polyalkoxyether phosphates, $C_{8-18}$ alcohol polyalkoxyether carboxylates, $C_{8-18}$ alcohol polyalkoxyether citrates, and/or alkyl benzenesulfonic acids neutralized to the inflection point in the titration curve with one or more basic compounds. The basic compound used to neutralize the different anionic surfactants may be the same or different.

In still other embodiments, the compositions of the invention comprise mixtures of at least two anionic surfactants selected from polyarylphenol polyalkoxyether sulfates, polyarylphenol polyalkoxyether phosphates, $C_{8-20}$ alkyl carboxylates including fatty acids, $C_{8-20}$ alcohol sulfates, $C_{8-20}$ alcohol phosphate mono- and diesters, $C_{8-20}$ alcohol and ($C_{8-20}$ alkyl)phenol polyoxyethylene ether carboxylates, sulfates and sulfonates, $C_{8-20}$ alcohol and ($C_{8-20}$ alkyl)phenol polyoxyethylene phosphate mono- and diesters, $C_{8-20}$ alkylbenzene sulfonates, naphthalene sulfonates and formaldehyde condensates thereof, lignosulfonates, $C_{8-20}$ alkyl sulfosuccinates and sulfosuccinamates, and/or $C_{8-20}$ acyl glutamates, sarcosinates, isethionates and taurates neutralized to the inflection point in the titration curve with one or more basic compounds. The basic compound used to neutralize the different anionic surfactants may be the same or different.

When neutralized, the anionic surfactants and basic compounds are preferably used in a ratio of about 1:1. One basic compound may be used to neutralize one or more anionic surfactants. In other embodiments, more than one basic compound may be used to neutralize one or more anionic surfactants.

Exemplary nonionic surfactants include ethylene oxide-propylene oxide block copolymers; ethylene oxide-butylene oxide block copolymers; $C_{2-6}$ alkyl adducts of ethylene oxide-propylene oxide block copolymers; $C_{2-6}$ alkyl adducts of ethylene oxide-butylene oxide block copolymers; polypropylene glycols; polyethylene glycols; polyarylphenol polyethoxy ethers; polyalkylphenol polyethoxy ethers; polyglycol ether derivatives of aliphatic or cycloaliphatic alcohols or of saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols; mono-, di- and tri($C_{12-20}$ alkyl)esters of polyoxyethylene sorbitan; alkoxylated vegetable oils; alkoxylated acetylenic diols; alkyl polyglycosides and mixtures thereof.

The ethylene oxide-propylene oxide block copolymers may comprise alkyl or alkyphenol ether bases, such as butyl ether, methyl ether, propyl ether, ethyl ether, or mixtures thereof. Commercially available nonionic surfactants include, for example, TOXIMUL® 8320 (Stepan Corporation, Northfield, Ill.) (butyl ether derivative of EO/PO block copolymer), WITCONOL® NS-500LQ (CK Witco Corporation, Greenwich, Conn.) (butyl ether derivative of EO/PO block copolymer) and WITCONOL® NS-108LQ (CK Witco Corporation, Greenwich, Conn.) (nonylphenol ether derivative of EO/PO block copolymer).

Any alkyl polyglycoside known in the art can be used in the invention. The alkyl polyglycoside of the invention may have formula (I):

$$R_1O(R_2O)_b(Z)_a \qquad (I)$$

$R_1$ is a monovalent organic radical having from about 6 to about 30 carbon atoms. $R_1$ is preferably a $C_{8-22}$ alkyl or alkenyl group, more preferably a $C_{8-11}$ alkyl group. $R_2$ is a divalent alkylene radical having from about 2 to about 4 carbon atoms. $R_2$ is preferably ethylene or propylene, more preferably ethylene. b is 0 to about 100. b is preferably 0 to about 12, more preferably 0. Z is a saccharide residue having about 5 to about 6 carbon atoms. Z may be glucose, mannose, fructose, galasctose, talose, gulose, altrose, allose, apiose, gallose, idose, ribose, arabinose, xylose, lyxose, or a mixture thereof. Z is preferably glucose. a is an integer from 1 to about 6. a is preferably from 1 to about 3, more preferably about 2.

Preferred compounds of formula (I) are compounds of formula (II):

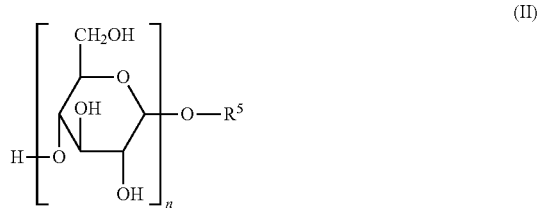

where n is the degree of polymerization and is from 1 to 3, preferably 1 or 2, and $R^5$ is a branched or straight chain alkyl group having from 4 to 18 carbon atoms or a mixture of alkyl groups having from 4 to 18 carbon atoms.

Exemplary alkyl polyglycosides include APG® 325 (Cognis Corporation, Cincinnati, Ohio) (an alkyl polyglycoside in which the alkyl group contains 9 to 11 carbon atoms and has an average degree of polymerization of 1.6), PLANTAREN® 2000 (Cognis Corporation, Cincinnati, Ohio) (an alkyl polyglycoside in which the alkyl group contains 8 to 16 carbon atoms and has an average degree of polymerization of 1.4), PLANTAREN® 1300 (Cognis Corporation, Cincinnati, Ohio) (an alkyl polyglycoside in which the alkyl group contains 12 to 16 carbon atoms and has an average degree of polymerization of 1.6), AGRIMUL® PG 2067 (Cognis Corporation, Cincinnati, Ohio) (an alkyl polyglycoside in which the alkyl group contains 8 to 10 carbon atoms and has an average degree of polymerization of 1.7), AGRIMUL® PG 2069 (Cognis Corporation, Cincinnati, Ohio) (an alkyl polyglycoside in which the alkyl group contains 9 to 11 carbon atoms and has an average degree of polymerization of 1.6), AGRIMUL® PG 2076 (Cognis Corporation, Cincinnati, Ohio) (an alkyl polyglycoside in which the alkyl group contains 8 to 10 carbon atoms and has an average degree of polymerization of 1.5), ATPLUS® 438 (Uniqema, Inc., Wilmington, Del.) (an alkylpolysaccharide in which the alkyl group contains 9 to 11 carbon atoms), and ATPLUS® 452 (Uniqema, Inc., Wilmington, Del.) (an alkylpolysaccharide in which the alkyl group contains 8 to 10 carbon atoms).

Cationic surfactants are preferably quaternary ammonium salts carrying, as N-substituent, at least one $C_8$-$C_{22}$ alkyl radical and, as further substituents, unsubstituted or halogenated lower alkyl, benzyl or hydroxy-lower alkyl radicals. The salts are preferably in the form of halides, methyl sulfates or ethyl sulfates, for example stearyl trimethylammonium chloride or benzyl bis(2-chloroethyl)ethylammonium bromide.

The amount of surfactant(s) depends on the particular active ingredients selected for the composition and the absolute and relative amounts of these desired. Suitable amounts of stabilizing system components selected from the classes or specific examples provided herein can be determined by routine experimentation, the test being that substantially no phase separation, sedimentation or flocculation is exhibited by the composition following storage at 20-25° C. for a period of 24 hours, or, for preferred embodiments, following a longer period of storage over a broader range of temperatures as indicated above. Typically the total concentration of all surfactants in the composition as a whole is about 1% to about 10% by weight, for example about 1.5% to about 5% by weight, excluding the weight of counterions, if present.

In computing relative amounts of surfactants present in a composition, the weight of water or other diluent supplied with a surfactant, if known, should be excluded. For example, WITCONATE® 79S of CK Witco Corporation contains 52% dodecylbenzene sulfonic acid triethanolamine salt. In a composition containing 1% WITCONATE® 79S, the concentration of dodecylbenzene sulfonic acid triethanolamine salt should be computed as 0.52%.

Other adjuvants commonly utilized in agricultural compositions include crystallization inhibitors, viscosity modifiers, suspending agents, spray droplet modifiers, pigments, antioxidants, foaming agents, light-blocking agents, compatibilizing agents, antifoam agents, sequestering agents, neutralizing agents and buffers, corrosion inhibitors, dyes, odorants, spreading agents, penetration aids, micronutrients, emollients, lubricants, sticking agents, dispersing agents, thickening agents, freezing point depressants, antimicrobial agents, and the like. The compositions can also contain other compatible components, for example, plant growth regulants, fungicides, insecticides, and the like and can be formulated with liquid fertilizers or solid, particulate fertilizer carriers such as ammonium nitrate, urea and the like.

The herbicidal compositions will usually comprise from 0.1 to 99% by weight, preferably from 0.1 to 95% by weight, of a mixture of the acetamide and the lipophilic additive, from 1 to 99.9% by weight of a solid or liquid formulation assistant, and from 0 to 25% by weight, preferably from 0.1 to 25% by weight, of a surfactant. Whereas it is customarily preferred to formulate commercial products as concentrates, the end user will normally use dilute formulations. The compositions may also comprise further ingredients, such as: stabilisers, e.g. where appropriate epoxidised vegetable oils (epoxidised coconut oil, rapeseed oil, or soybean oil); antifoams, typically silicone oil; preservatives; viscosity regulators; binders; and tackifiers; as well as fertilisers or other chemical agents. Particularly preferred formulations are made up as follows (%=per cent by weight; compound mixture means a mixture of the acetamide, the lipophilic additive and any co-herbicide, if present):

Emulsifiable Concentrates:

| Compound mixture: | 1 to 95%, preferably 60 to 90% |
| Surfactant: | 1 to 30%, preferably 5 to 20% |
| Liquid carrier: | 1 to 80%, preferably 1 to 35% |

Dusts:

| Compound mixture: | 0.1 to 10%, preferably 0.1 to 5% |
| Solid carrier: | 99.9 to 90%, preferably 99.9 to 99% |

Suspension Concentrates:

| | |
|---|---|
| Compound mixture: | 5 to 75%, preferably 10 to 50% |
| Water: | 94 to 24%, preferably 88 to 30% |
| Surfactant: | 1 to 40%, preferably 2 to 30% |

Wettable Powders:

| | |
|---|---|
| Compound mixture: | 0.5 to 90%, preferably 1 to 80% |
| Surfactant: | 0.5 to 20%, preferably 1 to 15% |
| Solid carrier: | 5 to 95%, preferably 15 to 90% |

Granulates:

| | |
|---|---|
| Compound mixture: | 0.1 to 30%, preferably 0.1 to 15% |
| Solid carrier: | 99.5 to 70%, preferably 97 to 85% |

Biological Examples

The synergistic effect of the combinations of the acetamides with the lipophilic additives is demonstrated in the following Examples.

The formulations tested are set forth in Table 1. All formulations contained benoxacor safener in a ratio of S-metolachlor to benoxacor of 20:1. The formulation types for the test formulations were either emulsifiable concentrates (EC) or oil-in-water emulsions (EW) and were prepared by techniques known to one skilled in the art.

TABLE 1

Formulations

| Example | Active Ingredient | Wt. % A.I. | Lipophilic Additive | Wt. % Additive | Formulation Type | Surfactant System |
|---|---|---|---|---|---|---|
| 1 | S-metolachlor | 68.5 | Isopar ® V | 12.4 | EC | A |
| 2 | S-metolachlor | 55.2 | Stearic acid | 1.8 | EC | B |
| 3 | S-metolachlor | 43.4 | Stearyl alcohol | 5.0 | EW | C |
| Std* | S-metolachlor | 82.4 | None | — | EC | A |

A: 45% nonylphenol polyoxyethylene ether sulfate, polyoxyethylene tallowamine salt
   25% polyoxyethylene polyoxypropylene nonylphenol ether
   30% aromatic petroleum hydrocarbon
B: 50% polyoxyethylene lauryl alcohol ether
   50% polyoxyethylene polyoxypropylene nonylphenol ether
C: 50% polyoxyethylene nonylphenol ether
   32% dodecylbenzenesulfonic acid, triethanolamine salt
   18% water Seeds of test species *Echinochloa crus-galli* were sown in plastic pots in a standard soil. Pots were immediately watered and placed in a greenhouse under controlled growing conditions. Between 18 and 24 hours after seeding the soil surface was sprayed with aqueous solutions of the test formulations at doses ranging between 3.75 and 150 g ai/ha at an application volume of 150 l/ha. Pots were subsequently maintained in a greenhouse under controlled growing conditions. After a test period of 12 to 14 days, growth of the test species was evaluated. Plant growth in each pot was visually compared to plant growth in pots that were not sprayed with a test solution. Herbicidal activity was recorded on a scale of 0 to 100:100% means complete damage of test species, 0% means no damage. A value of 90% represents good herbicidal action. Herbicidal activity data were used to calculate a linear regression plot of herbicidal activity against the log of herbicide dose for each test formulation. From the linear regression analysis, the herbicide dose (g ai/ha) required for 90% damage of the test species (ED90) was calculated for each test formulation. The herbicidal activity of each test formulation was compared to the herbicidal activity of a standard formulation (that is, one not containing a lipophilic additive according to the present invention) applied in the same greenhouse test by calculating the ratio (ED90 for the standard formulation/ED90 for test formulation). When the value of the activity ratio is >1.0 then the test formulation has greater herbicidal activity than the standard formulation. The Performance Factor is the average of the above-described ratios over the number of trials indicated in Table 2 as (#).

TABLE 2

Pre-emergent herbicidal activity of test formulations

| Example | Lipophilic Additive | Performance Factor |
|---|---|---|
| 1 | Isopar ® V | 1.24 (5) |
| 2 | Stearic acid | 1.12 (6) |
| 3 | Stearyl alcohol | 1.21 (3) |
| Std* | None | 1 |

It is clear, upon examination of Table 2 that the compositions of the present invention exhibit superior performance compared to the standard formulation as evidenced by the Performance Factors greater than 1.

Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims.

What is claimed is:

1. A herbicidal composition, comprising:
   a) metolachlor or S-metolachlor;
   b) a synergistically active amount of isoparaffinic hydrocarbon fluid, stearic acid or stearyl alcohol; and
   c) benoxacor.

2. The herbicidal composition of claim 1 wherein the ratio (wt/wt) of a) to b) is 90:1 to 1.5:1.

3. The herbicidal composition of claim 1 wherein the composition comprises a mixture of the (S) and (R) isomers of metolachlor in the ratio of 50-100% (S) to 50-0% (R).

4. The herbicidal composition of claim 1 wherein the hydrocarbon fluid contains less than 2.0 wt. % aromatic component.

5. The herbicidal composition of claim 1 wherein at least 95 wt. % of the carbon structures of the hydrocarbon fluids fluid have a carbon number distribution of from C13 to C20.

6. The herbicidal composition of claim 1 wherein the hydrocarbon fluid comprises a synthetic iso-paraffin fluid.

7. The herbicidal composition of claim 1 further comprising a co-herbicide.

8. A method of controlling undesired plant growth in the presence of cultivated plants, which comprises treating the cultivated plants, plant parts, seed or the locus thereof with a herbicidally effective amount of the herbicidal composition according to claim 1.

9. The method according to claim 8, wherein the cultivated plants are selected from the group consisting of cereals, rape, sugar beet, sugar cane, rice, maize, plantation crops, soybeans and cotton.

10. The method of claim 8 wherein the cultivated plants comprise transgenic plants or herbicidally tolerant plants created by conventional breeding.

11. The method according to claim 8 wherein the herbicidally effective amount of the composition is applied to the soil as a preemergent herbicide.

12. The method of claim 8, which further comprises treating the cultivated plants, plant parts, seed or the locus thereof with a co-herbicide.

13. The method of claim 12, which comprises treating the cultivated plants, plant parts, seed or the locus thereof at separate times with the herbicidal composition and the co-herbicide.

* * * * *